United States Patent [19]

Cairns et al.

[11] 4,335,048

[45] Jun. 15, 1982

[54] 5-(2-HYDROXYPROPOXY)-8-PROPYL-4H-1-BENZOPYRAN-4-ONE-2-CARBOXYLIC ACID

[75] Inventors: Hugh Cairns, Loughborough; Richard Hazard, Cropston; John King; Thomas B. Lee, both of Loughborough, all of England

[73] Assignee: Fisons Limited, London, England

[21] Appl. No.: 122,284

[22] Filed: Feb. 19, 1980

Related U.S. Application Data

[63] Continuation of Ser. No. 594,836, Jul. 10, 1975, abandoned.

[30] Foreign Application Priority Data

Jul. 10, 1974 [GB] United Kingdom ............... 30647/74

[51] Int. Cl.³ .......................................... C07D 311/24
[52] U.S. Cl. ..................................... 549/402; 424/283
[58] Field of Search .................................. 260/345.2

[56] References Cited

U.S. PATENT DOCUMENTS

| | | | |
|---|---|---|---|
| 3,427,324 | 2/1969 | Fitzmaurice | 260/345.2 |
| 3,484,445 | 12/1969 | Lee et al. | 260/345.2 |
| 3,519,652 | 7/1970 | Fitzmaurice et al. | 260/345.2 |
| 3,629,920 | 12/1971 | Cairns et al. | 260/345.2 |
| 3,652,765 | 3/1972 | Elli et al. | 260/345.2 |
| 3,686,320 | 8/1972 | Fitzmaurice et al. | 260/345.2 |
| 3,786,071 | 1/1974 | Cairns et al. | 260/345.2 |
| 3,860,617 | 1/1975 | Cairns et al. | 260/345.2 |

OTHER PUBLICATIONS 3966M 04001966 FRX 260 345.2

Primary Examiner—Nicky Chan
Attorney, Agent, or Firm—Merriam, Marshall & Bicknell

[57] ABSTRACT

There is described the compound of formula I,

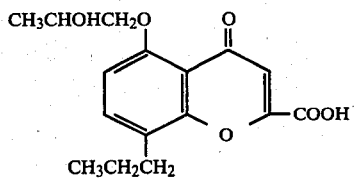

and pharmaceutically acceptable derivatives thereof. Processes for making the compound and pharmaceutical, e.g. anti-asthmatic, compositions containing it are also described.

2 Claims, No Drawings

5-(2-HYDROXYPROPOXY)-8-PROPYL-4H-1-BENZOPYRAN-4-ONE-2-CARBOXYLIC ACID

This is a continuation of application Ser. No. 594,836, filed July 10, 1975, now abandoned.

This invention relates to a new compound, processes for its preparation and compositions containing it.

According to our invention we provide the compound of formula I,

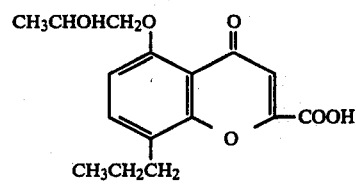

and pharmaceutically acceptable derivatives thereof.

According to our invention we also provide a process for the production of the compound of formula I, or a pharmaceutically acceptable derivative thereof, which comprises (a) cyclising a compound of formula II,

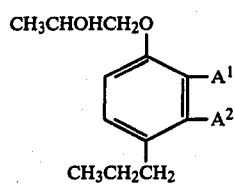

in which $A^1$ and $A^2$ represent the pairs of groups
(i) —COCH$_2$COCOR and —OM or Hal, or
(ii) —H and —O—C(COOM)=CH—COOM in which R represents —OM, or a group hydrolyseable thereto, M represents hydrogen or an alkali metal, and Hal represents a halogen atom, (b) selectively hydrolysing or oxidising a compound of formula III,

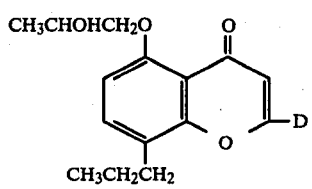

in which D represents a group which is hydrolyseable or oxidiseable to an —COOH group, (c) selectively dehydrogenating a compound of formula IV,

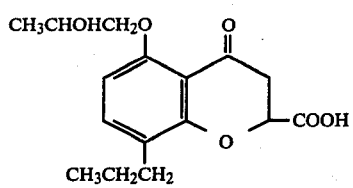

or an ester thereof, (d) selectively hydrogenating a compound of formula V,

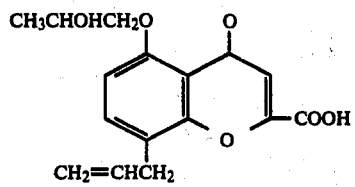

or an ester thereof, (e) conversion of a compound of formula VI,

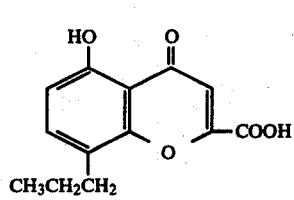

or an ester thereof, in which Ra and Rb, together with the carbon atom to which they are attached form a —CS— group, or together form a chain —S—(CH$_2$)$_n$—S—, in which n is 2 or 3, to a compound of formula I, or an ester thereof, (f) reaction of a compound of formula VII,

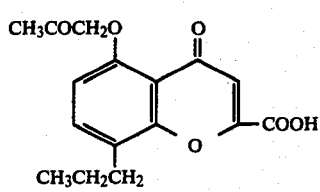

or an ester thereof, with propylene oxide, or a compound of formula VIII, $$CH_3CHOHCH_2X \qquad VIII$$

in which X represents a good leaving group, (g) selective reduction of a compound of formula IX,

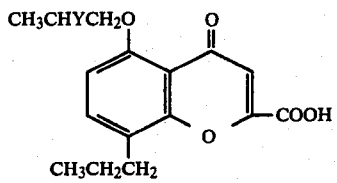

or an ester thereof, or (h) selective hydrolysis or hydrogenolysis of a compound of formula X,

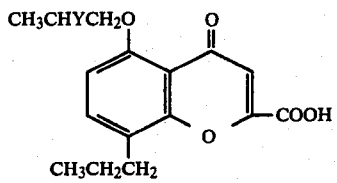

or an ester thereof, in which Y is a group hydrolyseable to an —OH group, and where desired or necessary converting the compound of formula I to a pharmaceutically acceptable derivative thereof or vice versa.

When $A_2$ is a group —OM the cyclisation of process (a)(i) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. The group —COR is preferably an ester group, e.g. R may be a lower alkoxy group. When $A_2$ is Hal the cyclisation may be carried out in a solvent which is inert under the reaction conditions, preferably a high boiling polar solvent, e.g. pyridine, dimethylformamide or hexamethylphosphoramide. The reaction is preferably carried out with the aid of a strong base, for example an alkali metal, e.g. sodium, hydride. The reaction is preferably carried out at a temperature of from about 80° to 200° C., in the absence of free oxygen, e.g. under an inert atmosphere such as nitrogen.

The cyclisation of process (a)(ii) may be carried out by treating the appropriate compound of formula II with a cyclising agent, for example a dehydrating agent such as chlorosulphonic, polyphosphoric or sulphuric acid. The reaction is preferably carried out under anhydrous conditions and may be carried out at a temperature of from about 0° to 100° C.

In process (b) the group D may be, for example an ester, acid halide, amide or a nitrile group, which may be hydrolysed to a —COOH group. The hydrolysis may be carried out using conventional techniques, for example under mildly basic conditions, e.g. using sodium carbonate, sodium bicarbonate, or under acidic conditions, e.g. a mixture of aqueous dioxan and hydrochloric acid, or hydrogen bromide in acetic acid. The hydrolysis may be carried out at a temperature of from about 25° to 120° C. depending on the compounds used. Alternatively the group D may be an alkyl, e.g. a lower alkyl (e.g. C1 to 10) such as methyl; an aralkenyl, e.g. styryl; an acyl, e.g. a lower alkanoyl such as acetyl; or an aldehyde, e.g. formyl group. The oxidation may be carried out using conventional techniques which do not otherwise modify the molecule, for example an alkyl group may be oxidised using selenium dioxide, e.g. under reflux in aqueous dioxan. Aralkenyl groups may be oxidised using, for example, neutral or alkaline potassium permanganate in aqueous ethanol, and acyl groups may be oxidised using, for example an aqueous hypochlorite, e.g. sodium hypochlorite. Aldehyde groups may be oxidised using, for example silver oxide.

In process (c) the dehydrogenation may be carried out by oxidation using a mild oxidising agent, for example selenium dioxide, palladium black, chloranil, lead tetraacetate or triphenyl methyl perchlorate. Alternatively the dehydrogenation may be carried out indirectly by halogenation followed by dehydrohalogenation, e.g. by treatment with N-bromosuccinimide or pyridinium bromide perbromide to yield the 3-bromo derivative which is subsequently dehydrobrominated. The reaction may be carried out in a solvent which is inert under the reaction conditions, e.g. a halogenated hydrocarbon, xylene, or glacial acetic acid. The reaction may be carried out at an elevated temperature, e.g. from 25° to 150° C.

In process (d) the hydrogenation may be carried out using catalytic hydrogenation, for example using a palladium on charcoal catalyst in a suitable solvent, e.g. ethanol. The reaction may conveniently be carried out at from about 20° to 80° C., preferably at slightly greater than atmospheric pressure.

In process (e), when Ra and Rb together form a chain —S—$(CH_2)_n$—S—, the conversion may comprise oxidative hydrolysis and may be carried out in an aqueous polar organic solvent, for example aqueous ethanol, acetone or tetrahydrofuran. The oxidative hydrolyses may be carried out in the presence of an oxidising agent, for example mercuric chloride, an N-halosuccinimide such as N-bromo- or N-chloro-succinimide, a per-acid such as periodic acid; or p-toluenesulphonchloramide or a salt thereof. When mercuric chloride is used the reaction may be carried out in the presence of a base, e.g. mercuric oxide, cadmium carbonate or calcium carbonate. N-halosuccinimides may be used alone or in the presence of a silver salt, e.g. silver perchlorate, or silver nitrate. The reaction may conveniently be carried out at a temperature of from about 15° to 100° C.

When Ra and Rb, together with the carbon atom to which they are attached form a —CS— group the conversion may comprise hydrolysis and may be carried out in the presence of a heavy metal compound, e.g. a compound of group Ib, IIb or IIIb of the Periodic Table of Mendeleef, as catalyst. Suitable compounds include mercury, thallium and silver compounds, e.g. mercury (II) acetate or chloride, thallium (III) trifluoroacetate, or silver oxide. The reaction may be carried out in the presence of water and an organic solvent system such as acetone-acetic acid, alkanols, tetrahydrofuran/methanol, or tetrahydrofuran. Alternatively the reaction may be carried out by alkylation followed by hydrolysis. In such cases the reaction may be effected by (i) an alkyl halide or sulphonate (e.g. methyl iodide) in a moist solvent, e.g. acetone, (ii) an alkylfluorosulphonate and water in sulphur dioxide, or (iii) a trialkyl oxonium fluoroborate followed by aqueous sodium hydroxide.

In process (f) the good leaving group X may be an anion forming group, for example, a halide, e.g. a bromide or iodide, or an alkyl or aryl sulphonate, e.g. a methane sulphonate group. The reaction may be carried out in a solvent which is inert under the reaction conditions, e.g. a lower alkanol, a ketone such as acetone or isobutylmethyl ketone, or dimethylformamide. The reaction may also be carried out in the presence of an acid binding agent, e.g. potassium carbonate, and optionally also in the presence of a catalyst, e.g. potassium iodide; suitably the reaction is carried out at a temperature of 25° to 150° C. When propylene oxide is used in process (f) the reaction may be carried out in the presence of a catalyst, e.g. benzyltrimethylammonium hydroxide. Alternatively process (f) may be carried out using the compound of formula VII (or preferably an ester thereof), in the form of a thallium salt of the reactive hydroxy group. When a thallium salt is used the reaction may be carried out at an elevated temperature and the product may be recovered from the reaction mixture by solvent extraction.

The reduction of process (g) may be carried out using a metal hydride, for example a borohydride such as sodium borohydride. The reaction may be carried out in a suitable solvent, for example water, bis(2-methoxyethyl)ether or a mixture thereof and may conveniently be carried out at a temperature of from about 0° to 40° C. Alternatively the reduction may be carried out using hydrogen and a catalyst, e.g. palladium on carbon. The catalytic reduction may be carried out in a suitable solvent, e.g. ethanol, at a temperature of from about 20° to 100° C.

In process (h) the group Y may be an ether group —ORx in which Rx may be a straight or branched alkyl group, preferably containing from 1 to 10 carbon atoms, e.g. a methyl or a t-butyl group. Alternatively the group Rx may be a phenylmethyl group, e.g. a benzyl or a triphenylmethyl group, in which the phenyl group is optionally substituted, e.g. by a nitro group. Alternatively the group —ORx may be part of a mixed acetal, for example —ORx may be a tetrahydropyranyl ether. The —ORx ether groups may be removed by treatment of the compound of formula X with acid in a solvent which is inert under the reaction conditions. Thus when Rx is a methyl or straight-chain alkyl group, the ether may be treated with an acid, for example hydrogen bromide, in for example water, glacial acetic acid or trifluoracetic acid, at a temperature of from 0° C. to the boiling point of the solvent employed. When Rx is a branched chain alkyl group, for example t-butyl, the ether may be treated with an acid, for example hydrogen chloride, in for example methanol, usually at about ambient temperature. When Rx is an phenylalkyl or substituted phenylalkyl group, the ether may be treated with an acid, for example hydrogen bromide, in for example water, glacial acetic acid or trifluoroacetic acid, at a temperature of from 0° C. to the boiling point of the solvent. Alternatively, the ether may be hydrogenolysed, for example in the presence of a palladium/carbon catalyst in for example ethanol or glacial acetic acid, at a temperature of from about 0° to 60° C. When Rx is part of a mixed acetal, the ether may be hydrolysed with an acid, for example 20% aqueous sulphuric acid, usually at about ambient temperature.

The group —ORx may also represent an ester group, for example of formula —OCORy, in which Ry may be hydrogen, an alkyl group preferably containing from 1 to 10 carbon atoms (e.g. methyl) and optionally substituted by halogen, (e.g. trifluoromethyl); or a phenyl group. The removal of the ester group may be carried out under acidic, or preferably under basic conditions, using for example, sodium carbonate or sodium hydroxide, in for example water or ethanol, at temperatures ranging from 0° C. to the boiling point of the solvent employed.

Y may also be a halogen atom, for example a chlorine atom, a diazo group, or a sulphonate group, for example a methane sulphonate or a p-toluene sulphonate group. The hydrolysis of the groups Y, which are not groups —ORx, may be carried out under mildly basic conditions, for example using sodium hydroxide in a solvent which is inert under the reaction conditions, e.g. water or ethanol. Alternatively, when the group Y is a diazo group, the hydrolysis may be carried out using water. The reaction may be carried out at a temperature of from about 0° C. to the boiling point of the solvent employed.

In processes (c) to (h) the ester may be, for example, a alkyl Cl to 10 ester, e.g. an ethyl ester.

The compounds of formula II in which $A^1$ and $A^2$ represent the pair of groups —COCH$_2$COCOR and —OM or Hal may be made by reacting a compound of formula XI,

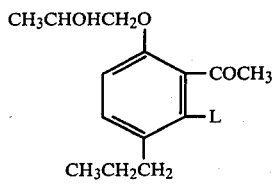

XI in which L represents a group —OM or Hal as defined above, with a compound of formula XII,

R'CZCZR  XII in which
R is as defined above,
R' is a suitable leaving group, e.g. an alkoxy, halo, amino, alkylamino, substituted amino (e.g. an arylsulphonylamino group) or substituted alkylamino group, reactive with the carbanation of the —COCH$_3$ group of the compound of formula XI,
each Z is a carbonyl oxygen atom, or one Z may represent two halogen atoms and the other a carbonyl oxygen atom,
and if necessary hydrolysing the resulting compound to a compound of formula II. The preferred compounds of formula XII, are dialkyl oxalates, e.g. diethyl oxalate.

The compound of formula II in which $A^1$ and $A^2$ represent the pair of groups —H and —O—C(—COOM)=CH—COOM may be made by reacting the compound of formula XIII,

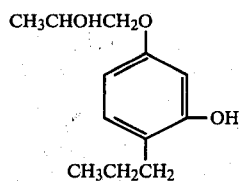

XIII with a dialkyl acetylene dicarboxylate, in conventional manner, followed if necessary by hydrolysis.

The compounds of formula III may be made in a manner analogous to process (a)(i) using a starting material of formula XIV,

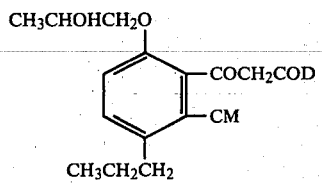

XIV in which D is as defined above.

The compounds of formula XIV may be made from known compounds in a manner analogous to that described above for the preparation of the corresponding compounds of formula II.

The compound of formula IV may be made by cyclising a compound of formula XV,

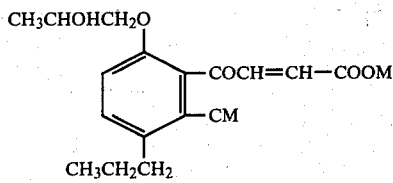

XV in which M is as defined above,
by treating the compound of formula XV with a base in a solvent which is inert under the reaction conditions.

The compounds of formula XV may be made by reacting a compound of formula XI, in which L is a group —OM, with glyoxalic acid or an ester thereof. Alternatively the compounds of formula XV may be made by reacting the compound of formula XIII with maleic anhydride in a solvent in the presence of a Lewis acid, e.g. AlCl₃, and decomposition of the resulting complex with dilute acid.

The compound of formula IV may also be made by selective hydrogenation of the compound of formula I.

The compounds of formulae V, VII, IX and X are either known or may be made from known compounds by processes analogous to process (a) above. Alternatively these compounds may be made from known compounds using techniques known per se.

Compounds of formula VI may be made from the compound of formula I or from known compounds using conventional techniques known per se.

The compound of formula I and the intermediates therefore may be isolated from their reaction mixtures using conventional techniques.

Pharmaceutically acceptable derivatives of the compound of formula I include pharmaceutically acceptable salts, esters and amides of the 2-carboxylic acid group. Suitable salts include ammonium, alkali metal (e.g. sodium, potassium and lithium) and alkaline earth metal salts (e.g. calcium or magnesium), and salts with suitable organic bases, e.g. salts with lower alkylamines such as methylamine or ethylamine, with substituted lower alkylamines, e.g. hydroxy substituted alkylamines or with simple monocyclic nitrogen heterocyclic compounds, e.g. piperidine or morpholine. Suitable esters include simple lower alkyl (e.g. Cl to 10 ) esters, esters derived from alcohols containing basic groups, e.g. di-lower alkyl (e.g. Cl to 10) amino substituted alkanols, and acyloxy alkyl esters, e.g. a lower acyl-lower ester, or a bis-ester derived from a di-hydroxy compound, e.g. a di(hydroxy-lower alkyl)ether. The pharmaceutically acceptable salts of the basic esters, e.g. the hydrochloride, may also be used. The esters may be made by conventional techniques, e.g. esterification or transesterification.

The compound of formula I, and pharmaceutically acceptable derivatives thereof, are useful because they possess pharmacological activity in animals; in particular they are useful because they inhibit the release and/or action of pharmacological mediators which result from the in vivo combination of certain types of antibody and specific antigen e.g. the combination of reaginic antibody with specific antigen (see Example 27 of British Patent Specification No. 1,292,601). In man, both subjective and objective changes which result from the inhalation of specific antigen by sensitised subjects are inhibited by prior administration of the new compounds. Thus the new compounds are useful in the treatment of asthma, e.g. allergic asthma. The new compounds are also useful in the treatment of so-called 'intrinsic' asthma (in which no sensitivity to extrinsic antigen can be demonstrated). The new compounds are also useful in the treatment of other conditions in which antigen-antibody reactions are responsible for disease, for example, hay fever; certain eye conditions, e.g. trachoma; and atopic eczema; and gastro-intestinal allergy, especially in children, e.g. milk allergy.

For the above mentioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example 27 of British Patent Specification No. 1,292,601. For man the indicated total daily dosage is in the range of from about 1 mg to 3,500 mg, preferably from about 500 mg to 2,000 mg, which may be administered in divided doses from 1 to 6 times a day or in sustained release form. Thus unit dosage forms suitable for administration (by inhalation or oesophageally) comprise from about 0.17 mg to 600 mg of the compound admixed with a solid or liquid pharmaceutically acceptable diluent, carrier or adjuvant.

The compound of formula I, and pharmaceutically acceptable derivatives thereof, (and in particular the free compound of formula I) have the advantage that they are more readily absorbed, or are less irritant to the GI tract, or have less toxic side effects, or are more active when administered oesophageally than compounds of similar structure to the compound of formula I.

According to the invention there is also provided a process for the production of a pharmaceutically acceptable salt of the compound of formula I, which comprises treating a compound of formula Ic,

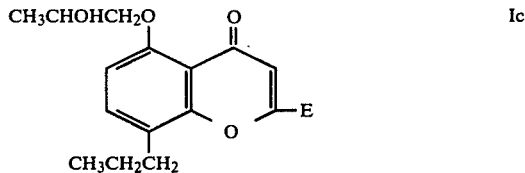

in which E is a carboxylic acid group (or an ester thereof, or another salt thereof), a nitrile group, an acid halide group or an amide group,
with a compound containing an available pharmaceutically acceptable cation and capable of converting the group E to a pharmaceutically acceptable salt of a carboxylic acid group.

Compounds capable of converting the group E to a pharmaceutically acceptable salt of a carboxylic acid group include compounds, e.g. bases and ion exchange resins, containing pharmaceutically acceptable cations, e.g. sodium, potassium, calcium, ammonium and appropriate nitrogen containing organic cations. In general we prefer to form the pharmaceutically acceptable salt by treating the free acid of formula I with an appropriate base, e.g. with an alkaline-earth or alkali metal hydroxide, carbonate or bicarbonate in aqueous solution or by a metathetical process. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

According to our invention we also provide a pharmaceutical composition comprising (preferably a minor proportion of) the compound of formula I, or a pharmaceutically acceptable derivative thereof, as active ingredient, in combination with a pharmaceutically acceptable adjuvant, diluent or carrier. Examples of suitable adjuvants, diluents or carriers are:—for tablets and dragées; lactose, starch, talc or stearic acid; for capsules, tartaric acid or lactose; for suppositories; natural or hardened oils or waxes; for inhalation compositions, coarse lactose. For use in inhalation, and other, compositions the compound of formula I, or the pharmaceutically acceptable derivative thereof, preferably has a mass median diameter of from 0.01 to 10 microns. The compound of such particle size may be made by grinding or milling followed if necessary by particle size classification using, for example a sieve. The compositions may also contain suitable preserving, stabilising, and wetting agents, solubilizers, sweetening and colouring agents and flavourings. The compositions may, if desired, be formulated in sustained release form. We prefer compositions which are designed to be taken oesophageally and to release their contents in the gastrointestinal tract.

The compound of formula I exists in optically active forms. The invention also provides the optical isomers of the compound of formula I, and mixtures, including racemic mixtures, thereof. The compound may be resolved into its optical isomers using conventional techniques.

The invention is illustrated, but in no way limited by the following Examples.

EXAMPLE 1

5-(2-Hydroxy-n-propoxy)-4-oxo-8-n-propyl-4H-1-benzopyran-2-carboxylic acid (a)
2-Hydroxy-6-(2-hydroxy-n-propoxy)-3-n-propylacetophenone A solution of 7.5 parts of 3-allyl-2-hydroxy-6-(2-hydroxy-n-propoxy)acetophenone in 120 parts of ethanol was treated with 0.5 parts of 5% palladium-on-charcoal catalyst. The mixture was shaken and exposed to a pressurised atmosphere of hydrogen (45 p.s.i.) for one hour at room temperature, then, after due precautions, the catalyst was filtered off and the ethanol was evaporated to leave 7.2 parts of 2-hydroxy-6-(2-hydroxy-n-propoxy)-3-n-propylacetophenone.

Analysis: Found: C, 66.0; H, 7.97. $C_{14}H_{20}O_4$ require: C, 66.7; H, 7.93%.

(b)
5-(2-Hydroxy-n-propoxy)-4-oxo-8-n-propyl-4H-1-benzopyran-2-carboxylic acid

To a solution of sodium ethoxide, prepared by dissolving 1.9 parts of sodium in 50 parts of ethanol, was added a solution of 5.0 parts of 2-hydroxy-6-(2-hydroxy-n-propoxy)-3-n-propylacetophenone and 7.3 parts of diethyl oxalate in 70 parts of diethyl ether. The mixture was stirred and heated under reflux for 18 hours then it was cooled, poured into 200 parts of ether and the mixture was extracted by swirling with 3 lots of 100 parts of water. The total aqueous extract was acidified with concentrated hydrochloric acid, then it was extracted with 3 lots of 70 parts of chloroform. The total chloroform extract was evaporated and the residual brown oil was heated under reflux for one hour with 45 parts of ethanol and 5 parts of concentrated hydrochloric acid. The solvent was then evaporated off and the residual oil was heated under reflux for 20 minutes with a mixture of 10 parts of methanol, 90 parts of water and 10 parts of sodium bicarbonate. The methanol was evaporated off and the remaining aqueous solution was filtered then acidified with concentrated hydrochloric acid. An oil was precipitated which was extracted into 50 parts of ether. The ethereal solution was dried over anhydrous magnesium sulphate, filtered and evaporated to leave 2.0 parts of 5-(2-hydroxy-n-propoxy)-4-oxo-8-n-propyl-4H-1-benzopyran-2-carboxylic acid hemihydrate as a pale brown solid, melting point 135°–137° C.

Analysis: Found: C, 60.45; H, 5.71. $C_{16}H_{18}O_5.\frac{1}{2}H_2O$ requires: C, 60.9; H, 6.04%.

(c) Sodium 5-(2-hydroxy-n-propoxy)-4-oxo-8-n-propyl-4H-1-benzopyran-2-carboxylate A solution of 2.0 parts of 5-(2-hydroxy-n-propoxy)-4-oxo-8-n-propyl-4H-1-benzopyran-2-carboxylic acid hemi-hydrate and 0.53 parts of sodium bicarbonate in 20 parts of water was prepared, filtered and freeze-dried to leave 2.1 parts of sodium 5-(2-hydroxy-n-propoxy)-4-oxo-8-n-propyl-4H-1-benzopyran-2-carboxylate as a pale brown powder.

EXAMPLE 2

To a stirred solution of sodium borohydride (0.4 g) in 0.02 N aqueous sodium hydroxide (30 ml) was added dropwise a solution of 5-(2-oxo-propoxy)-4-oxo-8-propyl-4H-1-benzopyran-2-carboxylic acid (2.3 g) in 0.02 N aqueous sodium hydroxide (100 ml). The resulting solution was stirred at ambient temperature for 20 hours, then cooled in ice and acidified with dilute hydrochloric acid.

The precipitate thus produced was filtered, washed with water and dried giving 5-(2-hydroxypropoxy)-4-oxo-8-propyl-4H-1-benzopyran-2-carboxylic acid. m.p. 134°–136° C.

EXAMPLE 3

5 -(2-Hydroxypropoxy)-2-methyl-4-oxo-8-propyl-4H-1-benzopyran (2.6 g) and selenium dioxide (1.1 g) were dissolved in 20% aqueous dioxan (150 ml) and heated at reflux for 24 hours. The suspension was filtered and the dioxan removed in vacuo. The residue was dissolved in chloroform (100 ml) and the chloroform solution extracted with saturated aqueous sodium bicarbonate. The bicarbonate extract was acidified with dilute hydrochloric acid and the resulting precipitate filtered off, washed with water and dried. Crystallisation from acetone gave 5-(2-hydroxypropoxy-4H-1-benzopyran-2-carboxylic acid. mp 135°–137° C.

EXAMPLE 4

A mixture of 5-(2-hydroxypropoxy)-8-propyl-4-thioxo-4H-1-benzopyran-2-carboxylic acid (0.025 g), methyl iodide (3 drops), acetone (10 ml) and water (4 drops) was stirred in the dark at ambient temperature for 2 days. Concentration of the reaction mixture gave a light brown solid which on crystallisation from acetone gave 5-(2-hydroxypropoxy) carboxylic acid. mp 133°–135° C.

EXAMPLE 5

A solution of 5-(2-hydroxypropoxy)-8-propyl-4-spiro-2-′-(1′,3′-dithiane)-4H-1-benzopyran-2-carboxylic acid (0.1 g) and per-iodic acid (0.1 g) in a mixture of acetone (15 ml) and water (5 ml) was stirred at ambient temperature for 2 hours. Removal of the acetone in vacuo produced a solid which was washed with water and dried giving 5-(2-hydroxypropoxy)-4-oxo-8-propyl-4H-1-benzopyran-2-carboxylic acid. mp 133°–135° C.

EXAMPLE 6

A mixture of 5-(2-hydroxypropoxy)-4-oxo-8-propyl-4H-1-benzopyran-2-carbonitrile (1.0 g), dioxan (20 ml) and dilute hydrochloric acid (20 ml) was heated at reflux for 24 hours. The dioxan was evaporated and the reaction mixture extracted with chloroform (100 ml).

The chloroform solution was extracted with saturated aqueous sodium bicarbonate (50 ml) and then the bicarbonate extract acidified with dilute hydrochloric acid. The resulting precipitate was filtered off, washed with water and dried giving 5-(2-hydroxypropoxy)-4-oxo-8-propyl-4H-1-benzopyran-2-carboxylic acid. mp 135°–137° C.

EXAMPLE 7

A suspension of 5-(2-hydroxypropoxy)-4-oxo-8-propyl-4H-1-benzopyran-2-carboxamide (1.0 g) in 1 N sodium hydroxide solution (50 ml) was heated at reflux until a homogeneous solution was obtained. Acidification with dilute hydrochloric acid gave a precipitate which was filtered off, washed with water and dried giving 5-(2-hydroxypropoxy)-4-oxo-8-propyl-4H-1-benzopyran-2-carboxylic acid. mp 135°–137° C.

EXAMPLE 8

To a solution of ethyl 5-(2-iodopropoxy)-4-oxo-8-propyl-4H-1-benzopyran-2-carboxylate (0.1 g) in 50% aqueous dioxan (15 ml) was added silver perchlorate (0.08 g). The solution was heated at reflux for 4 hours, filtered and evaporated to dryness. The brown, solid residue was crystallised from ethanol giving ethyl 5-(2-hydroxypropoxy)-4-oxo-8-propyl-4H-1-benzopyran-2-carboxylate identical in all respects with authentic material.

EXAMPLE 9

A solution of 5-(2-formyoloxypropoxy)-4-oxo-8-propyl-4H-1-benzopyran-2-carboxylic acid (0.1 g) in 5% aqueous sodium bicarbonate (10 ml) was heated on a steam bath for 2 hours. The solution was cooled, acidified with dilute hydrochloric acid and the resulting precipitate filtered off, washed with water and dried giving 5-(2-hydroxypropoxy)-4-oxo-8-propyl-4H-1-benzopyran-2-carboxylic acid. mp 134°–136° C.

EXAMPLE 10

A suspension of 5-[2-(tetrahydropyran-2-yloxy)propoxy]-4-oxo-8-propyl-4H-1-benzopyran-2-carboxylic acid (0.12 g) in ethanol (3 ml), water (2 ml) and concentrated hydrochloric acid (1 drop) was stirred for 15 minutes at ambient temperature. The mixture was then extracted with chloroform (3×20 ml) and the chloroform extracts bulked, dried and evaporated in vacuo. The residue was crystallised from acetone giving 5-(2-hydroxypropoxy)-4-oxo-8-propyl-4H-1-benzopyran-2-carboxylic acid m.g. 134°–135° C.

EXAMPLE 11

To a suspension of ethyl 8-allyl-5-(2-hydroxypropoxy)-4-oxo-4H-1-benzopyran-2-carboxylate (1.2 g) in ethanol (50 ml) was added 5% palladium on charcoal (0.2 g). The resulting suspension was then hydrogenated at a pressure of 4 atmospheres. After 30 minutes hydrogen uptake had ceased. The reaction mixture was filtered and the filtrate evaporated in vacuo. The residual solid was crystallised from ethanol giving ethyl 5-(2-hydroxypropoxy)-4-oxo-8-propyl-4H-1-benzopyran-2-carboxylate identical in all respects with authentic material.

EXAMPLE 12

A mixture of ethyl 5-hydroxy-4-oxo-8-propyl-4H-1-benzopyran-2-carboxylate (2.2 g), 2-hydroxy propyl bromide (5 g), anhydrous potassium carbonate (5 g) and acetone (200 ml) was heated at reflux for 3 days. After cooling, the reaction mixture was filtered and the acetone removed from the filtrate in vacuo. The oily residue was dissolved in chloroform (100 ml) and the chloroform solution washed with 1 N aqueous sodium hydroxide solution (50 ml) and water (50 ml) and then dried. Removal of the chloroform in vacuo gave a brown solid which on crystallisation from ethanol gave ethyl 5-(2-hydroxypropoxy)-4-oxo-8-propyl-4H-1-benzopyran-2-carboxylate identical in all respects with authentic material.

EXAMPLE 13

A mixture of 3-(2-hydroxypropoxy)-6-propylphenol (5 g); dimethyl acetylene dicarboxylate (3.55 g) and Triton 'B' (4 drops) was heated on a steam bath for 16 hours. Water (50 ml) was added and the resulting suspension extracted with chloroform (3×100 ml). The chloroform extracts were bulked, dried and then evaporated in vacuo.

The resulting oil was suspended in 5 N aqueous sodium hydroxide (100 ml) and heated at reflux until a homogeneous solution was obtained. After cooling, the solution was acidified with dilute hydrochloric acid and then extracted with chloroform (3×100 ml). The chloroform extracts were bulked, dried and then evaporated in vacuo.

The resulting oil was dissolved in chlorosulphonic acid (10 ml) and the solution stirred at ambient temperature for 1 hour before pouring onto ice/water (500 g). The precipitate was filtered off, washed with water, dried and crystallised from acetone giving 5-(2-hydroxypropoxy)-4-oxo-8-propyl-4H-1-benzopyran-2-carboxylic acid. mp 135°–137° C.

EXAMPLE 14

A mixture of ethyl 2,3-dihydro-5-(2-hydroxypropoxy)-4-oxo-8-propyl-4H-1-benzopyran-2-carboxylate and N-bromosuccinimide (1.1 g) was heated at reflux in carbon tetrachloride (100 ml) for 6 hours. The solution was cooled, washed with water, dried and evaporated. The solid residue was crystallised from ethanol giving ethyl 5-(2-hydroxypropoxy)-4-oxo-8-propyl-4H-1-benzopyran-2-carboxylate identical in all respects with authentic material.

EXAMPLE 15

To a solution of 2-bromo-6-(2-hydroxypropoxy)-3-propyl acetophenone (7.5 g) in dry dimethylformamide (50 ml) was added ether washed sodium hydride (1.81 g) and a solution of ethyl potassium oxalate (7.8 g) in dry dimethylformamide (200 ml). The resulting suspension was stirred at ambient temperature for 3 days. The reaction mixture was poured into dilute hydrochloric acid and the resulting suspension extracted with chloroform (3×100 ml). The chloroform extracts were bulked, dried and evaporated.

The resulting oil was dissolved in dimethyl formamide (50 ml) and added to a mixture of ether washed sodium hydride (1.81 g) in dry dimethyl formamide (50 ml). This mixture was heated, under nitrogen, at 150° C. for 5 hours, cooled and then poured into dilute hydrochloric acid. The solution was extracted with chloroform (3×100 ml) and the chloroform extracts bulked, washed with water, dried and evaporated. Trituration of the resulting oil gave a solid which on crystallisation from acetone gave 5-(2-hydroxypropoxy)-4-oxo-8-propyl-4H-1-benzopyran-2-carboxylic acid. mp 134°–135° C.

EXAMPLE A

| Tablet | |
|---|---|
| Compound of formula I | 500 mg |
| Binder, e.g. powdered tragacanth | 1 to 3% |
| Lubricant, e.g. magnesium stearate | 0.25 to 1% |
| Disintegrating agent, e.g. potato starch | 5 to 10% |
| Surfactant, e.g. di-octylsodium sulphosuccinate | 0.25% |

EXAMPLE B

| Capsule (Hard) | |
|---|---|
| Compound of formula I | 500 mg |
| Granulating agent, e.g. gum or starch mucilage | q.s. |
| Lubricant, e.g. magnesium stearate | 0.25 to 1% |

EXAMPLE C

| Capsule (Soft) | |
|---|---|
| Compound of formula I | 500 mg |
| Polyethylene glycol 400 | q.s. |
| Non-ionic surfactant, e.g. poloxyethylene sorbitan mono-oleate | q.s. |

EXAMPLE D

| Suppository | |
|---|---|
| Compound of formula I | 500 mg |
| Basis, e.g. polyethylene glycol 6,000 | 1 g |

We claim:
1. A compound selected from the group consisting of the compound having the formula

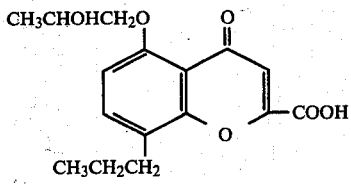

and pharmaceutically acceptable salts and C1–C10 alkyl esters thereof.

2. The compound having the formula

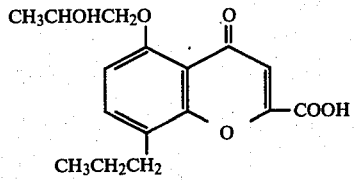

* * * * *

UNITED STATES PATENT AND TRADEMARK OFFICE
CERTIFICATE OF CORRECTION

PATENT NO. : 4,335,048
DATED : June 15, 1982
INVENTOR(S) : HUGH CAIRNS, ET AL.

It is certified that error appears in the above-identified patent and that said Letters Patent are hereby corrected as shown below:

Column 6, in the formula beginning at line 38, substituent "—CM" should be

-- —OM--

Column 6, in the formula beginning at line 54, substituent "—CM" should be

-- —OM--

Signed and Sealed this

Twenty-first Day of September 1982

[SEAL]

Attest:

GERALD J. MOSSINGHOFF

Attesting Officer

Commissioner of Patents and Trademarks